United States Patent
Miyamoto et al.

(10) Patent No.: US 9,513,295 B2
(45) Date of Patent: Dec. 6, 2016

(54) METHOD FOR DETECTING PROTEIN THAT INTERACTS WITH TARGET SUBSTANCE

(71) Applicant: TOKYO UNIVERSITY OF SCIENCE FOUNDATION, Tokyo (JP)

(72) Inventors: Etsuko Miyamoto, Tokyo (JP); Shigeo Fujimori, Tokyo (JP)

(73) Assignee: TOKYO UNIVERSITY OF SCIENCE FOUNDATION, Tokyo (JP)

(*) Notice: Subject to any disclaimer, the term of this patent is extended or adjusted under 35 U.S.C. 154(b) by 399 days.

(21) Appl. No.: 14/347,707

(22) PCT Filed: Sep. 28, 2012

(86) PCT No.: PCT/JP2012/075152
§ 371 (c)(1),
(2) Date: Mar. 27, 2014

(87) PCT Pub. No.: WO2013/047785
PCT Pub. Date: Apr. 4, 2013

(65) Prior Publication Data
US 2014/0243209 A1 Aug. 28, 2014

(30) Foreign Application Priority Data
Sep. 28, 2011 (JP) .................................. 2011-213424

(51) Int. Cl.
*C40B 30/04* (2006.01)
*G01N 33/68* (2006.01)
(Continued)

(52) U.S. Cl.
CPC ....... *G01N 33/6818* (2013.01); *C12N 15/1034* (2013.01); *C12N 15/1062* (2013.01); *C40B 30/04* (2013.01)

(58) Field of Classification Search
None
See application file for complete search history.

(56) References Cited

U.S. PATENT DOCUMENTS

2002/0072087 A1 6/2002 Yanagawa et al.
2008/0312103 A1 12/2008 Nemoto et al.

FOREIGN PATENT DOCUMENTS

WO 98/16636 4/1998
WO 03/048363 6/2003
(Continued)

OTHER PUBLICATIONS

Miyamoto-Sato et al., "Cell-free cotranslation and selection using in vitro virus for high-throughput analysis of protein-protein interactions and complexes", Genome Research, Mar. 2005, pp. 710-717.
(Continued)

*Primary Examiner* — Samuel Woolwine
*Assistant Examiner* — Kaijiang Zhang
(74) *Attorney, Agent, or Firm* — Wenderoth, Lind & Ponack, L.L.P.

(57) ABSTRACT

The present invention provides a method for detecting an interaction, which method can solve not only the problem of false negatives but also the problem of false positives. This method is a method for detecting a protein(s) that interact(s) with a target substance(s), the method comprising repeating a (1) transcription step, (2) assignment step, (3) selection step, and (4) amplification step, wherein: (a) in each of a plurality of times of preparation of a cDNA library among the initial preparation of a cDNA library and the round(s) of preparation of a cDNA library in the later amplification step(s), the cDNA library is prepared using a primer(s) having a sequence(s) specific to the time of preparation; (b) the cDNA libraries prepared using the primers having sequences specific to the times of preparation are mixed, and sequences in the cDNA library mixture are determined; (c) the determined sequences are subjected to measurement of the number(s) of molecules encoding the same candidate protein(s) for each time of preparation based on the sequence(s) specific to the time of preparation; and (d) a candidate protein(s) encoded by a molecule(s) that significantly increase(s) as the preparation rounds proceed is/are detected as the protein(s) that interact(s) with the target substance(s).

8 Claims, 2 Drawing Sheets

(51) Int. Cl.
*C12N 15/10* (2006.01)
*C12Q 1/68* (2006.01)

(56) References Cited

FOREIGN PATENT DOCUMENTS

WO 2004/053127 6/2004
WO 2006/041194 4/2006

OTHER PUBLICATIONS

Kosugi et al., "Six Classes of Nuclear Localization Signals Specific to Different Binding Grooves of Importin α", Journal of Biological Chemistry, vol. 284, No. 1, Jan. 2009, pp. 478-485.
Miyamoto-Sato et al., "A Comprehensive Resource of Interacting Protein Regions for Refining Human Transcription Factor Networks", PLoS ONE, vol. 5, Feb. 2010, pp. 1-11, e9289.
Fullwood et al., "Next-generation DNA sequencing of paired-end tags (PET) for transcriptome and genome analyses", Genome Research, 2009, vol. 19, pp. 521-532.
Horisawa et al., "Use of cDNA Tiling Arrays for Identifying Protein Interactions Selected by In Vitro Display Technologies", PLoS ONE, vol. 3, Feb. 2008, pp. 1-6, e1646.
Horisawa et al., "Application of Quantitative Real-Time PCR for Monitoring the Process of Enrichment of Clones on in Vitro Protein Selection", J. Biochem., vol. 137, No. 2, 2005, pp. 121-124.
International Search Report issued Oct. 30, 2012 in International (PCT) Application No. PCT/JP2012/075152.
International Preliminary Report on Patentability issued Apr. 1, 2014 and English translation of Written Opinion of the International Searching Authority issued Oct. 30, 2012 in International (PCT) Application No. PCT/JP2012/075152.
Extended European Search Report issued May 19, 2015 in corresponding European Application No. 12834742.4.
Morozova et al., "Applications of next-generation sequencing technologies in functional genomics", Genomics, vol. 92, No. 5, Aug. 24, 2008, pp. 255-264.
Ohashi et al., "Analysis of Transcription Factor Networks Using IVV Method", Methods in Molecular Biology, vol. 1164, 2014, pp. 15-22.

METHOD FOR DETECTING PROTEIN THAT INTERACTS WITH TARGET SUBSTANCE

TECHNICAL FIELD

The present invention relates to a method for detecting a protein that interacts with a target substance.

BACKGROUND ART

As a method for detecting an interaction between a protein and a substance, a method wherein mRNA-protein assignment molecules prepared by linking mRNAs to the proteins encoded thereby via covalent bonds are used for obtaining the amino acid sequence information of the protein as base sequence information of DNA is known as the in vitro virus (IVV) method (Patent Documents 1 to 3). By using the IVV method and a Sanger-type DNA sequencer, proteome analysis has been carried out (Non-patent Document 2, Non-patent Document 3 and Non-patent Document 4). Since, in the conventional Sanger-based sequence analysis, sequence analysis was possible for data corresponding to only a part (about 1000 reads) of the library, it has been practically difficult to cover the whole library space (false-negative problem).

Attempts have been made to introduce a next-generation sequencer to transcriptome and proteome analyses to obtain a large amount of information on intermolecular interactions among proteins/DNAs/RNAs (Non-patent Document 4). However, it is known that false positives are contained in the obtained data, and that acquisition of a large amount of data results in acquisition of a large amount of false-positive data. Therefore, elimination of the false positives (improvement of reliability) has been demanded.

PRIOR ART DOCUMENTS

Patent Documents

Patent Document 1: WO 98/16636
Patent Document 2: WO 2003/048363
Patent Document 3: WO 2004/053127

Non-Patent Documents

Non-patent Document 1: Genome Res., 15, 710-717, 2005
Non-patent Document 2: J Biol Chem, 284, 478-485, 2009
Non-patent Document 3: PLoS ONE, 5, e9289, 2010
Non-patent Document 4: Genome Res, 19, 521-532, 2009

SUMMARY OF THE INVENTION

By combining the IVV method and the next-generation sequencer, sequence analysis for 100,000 to 100,000,000 reads is possible, and remarkable improvement of the past false-negative problem (problem of failure to analyze sequence data in the library) can be expected. However, since large-scale sequence analysis also produces a large amount of false-positive data, it is very important to solve not only the problem of false negatives but also the problem of false positives.

The present invention aims to provide a method for detecting an interaction, which method can solve not only the problem of false negatives but also the problem of false positives.

The present inventors hypothesized that the problem of false positives can be solved if enrichment of the protein of interest in each round can be detected in the absence of influence of its absolute amount in the library, and discovered that such detection is possible by carrying out sequence analysis of a sample prepared by a specific mode utilizing properties of the IVV method, thereby completing the present invention.

The present invention provides the following method.

A method for detecting a protein(s) that interact(s) with a target substance(s), the method comprising:

(1) a transcription step of transcribing a cDNA library encoding a candidate protein(s) to prepare an mRNA library;

(2) an assignment step of preparing an mRNA-protein assignment molecular library from the mRNA library prepared in the transcription step;

(3) a selection step of selecting an mRNA-protein assignment molecule(s) that interact(s) with a target substance(s) from the mRNA-protein assignment molecular library prepared in the assignment step;

(4) an amplification step of preparing a cDNA library encoding the candidate protein(s) by nucleic acid amplification based on the mRNA portion(s) of the mRNA-protein assignment molecule(s) selected in the selection step; and (5) repeating Steps (1) to (4) using the cDNA library prepared in the amplification step;

wherein the method comprises:

(a) preparing, in each of a plurality of times of preparation of a cDNA library among the initial preparation of a cDNA library and the round(s) of preparation of a cDNA library in the later amplification step(s), the cDNA library using a primer(s) having a sequence(s) specific to the time of preparation;

(b) mixing the cDNA libraries prepared using the primers having sequences specific to the times of preparation, and determining sequences in the cDNA library mixture;

(c) subjecting the determined sequences to measurement of the number(s) of molecules encoding the same candidate protein(s) for each time of preparation based on the sequence(s) specific to the time of preparation; and (d) detecting, as the protein(s) that interact(s) with the target substance(s), a candidate protein(s) encoded by a molecule(s) that significantly increase(s) as the preparation rounds proceed.

In the method of the present invention, the mixing ratio of the cDNA library obtained by an earlier time of preparation is preferably not less than the mixing ratio of the cDNA library obtained by the subsequent time of preparation.

The sequence specific to each time of preparation usually has a length of 4 to 10 bases.

The primer usually has the sequence specific to the time of preparation at the 5'-end.

The number of cDNA libraries mixed in Step (b) is usually not less than 3.

The cDNA libraries mixed in Step (b) may comprise the initial cDNA library.

The increase in the molecules in Step (d) is preferably evaluated by a statistical method.

For example, the target substance is a protein. In cases of a protein, protein-protein interaction can be detected.

Effect of the Invention

The present invention provides a method in which the problems of false negatives and false positives are reduced. By the present invention, molecules encoding a protein in a small absolute amount, contained in a library, can be detected. In contrast to conventional methods, in which a verification experiment by large-scale real-time PCR or the like is required for eliminating false positives, the method of the present invention does not require such a verification experiment. Therefore, not only an increased reliability of data, but also significant reduction in the time required for the experiment and in the cost can be achieved.

BRIEF DESCRIPTION OF THE DRAWINGS

FIG. 1 illustrates a summary of Example of the method of the present invention. First, a prey cDNA library is prepared using initial amplification primers (1), and in vitro transcription is carried out (2). The puromycin attached to the prey mRNA after the transcription is incorporated into a ribosome upon synthesis of the protein encoded by the mRNA, and bound to the C-terminus [formation of an IVV molecule] (3). Subsequently, a prey that binds to a bait protein is selected using affinity beads (4), and RT-PCR is carried out to perform DNA transcription and amplification using an amplification primer(s) specific to the time of amplification (5). By repeating these steps (rounds), the prey sequence can be enriched. The prey mRNA after each round is amplified using a primer(s) having a sequence(s) unique to the time of amplification (round) (bar-code sequence), and a part of each amplification product is stored (5'). The resulting products are mixed together (6), and sequencing with a high-speed sequencer is carried out for the mixture (7), followed by subjecting each determined sequence to restoration of the round information and mapping on the genomic sequence (8). Finally, significance of the level of increase in the prey is confirmed by a statistical test, to evaluate the interaction (9).

MODE FOR CARRYING OUT THE INVENTION

Figure 1:
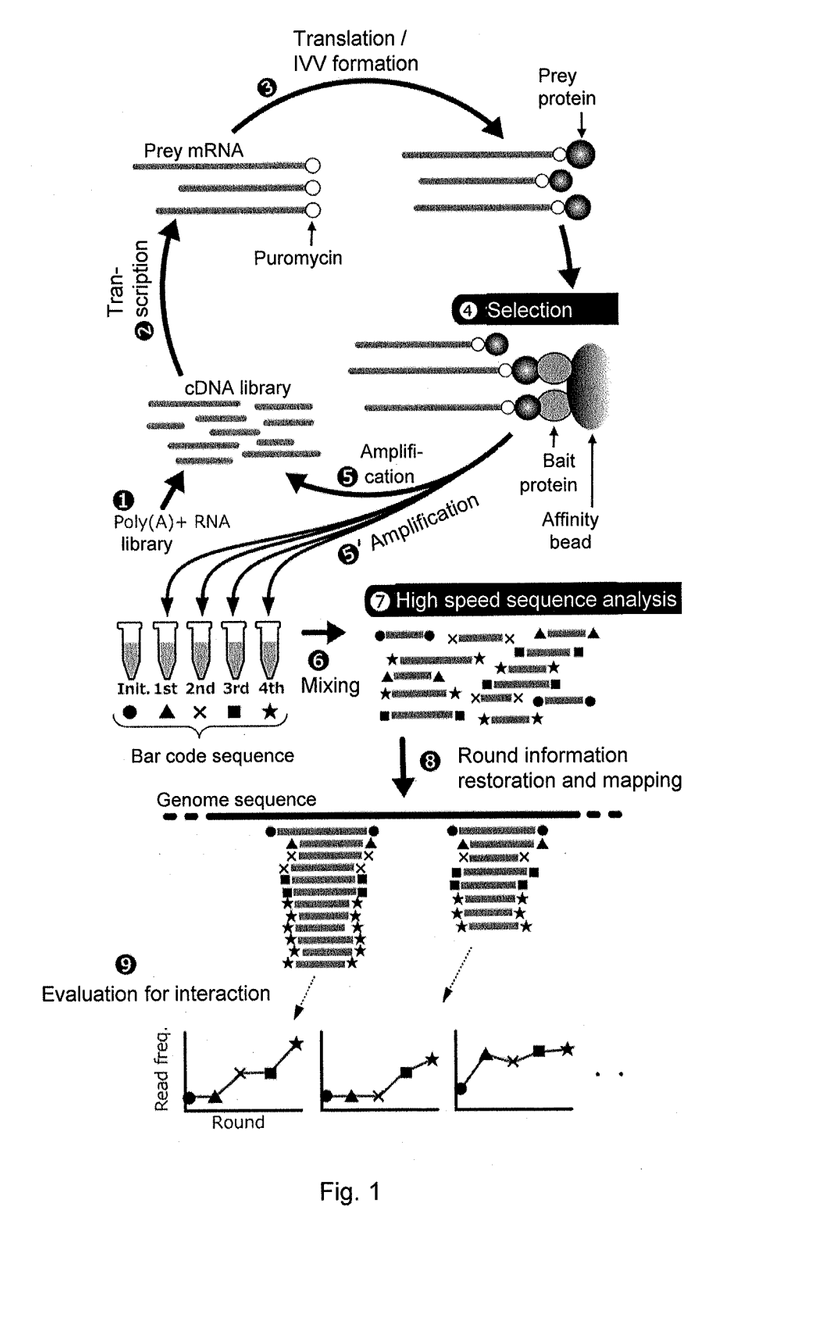

In the method of the present invention, screening by the WV method and sequence analysis are combined (FIG. 1). The first part may be the same as the conventional method based on the IVV method except for preparation of a cDNA library by amplification using a specific primer(s). In the second part, sequence analysis is carried out using a sequence(s) contained in the specific primer(s).

First, the first part, screening, is explained. This part may be basically the same as the process of detection of PPIs using IVV. This process can be further divided into several parts—that is, transcription of mRNA from a cDNA library; formation of IVV, which is usually composed of ligation of a PEG-Puro spacer to the mRNA, and translation (assignment); selection; and amplification for preparation of the cDNA library to be used in the subsequent round. These in vitro steps are repeated (for usually about 3 to 5 rounds) to allow gradual enrichment of prey molecules that bind to the bait in the library, and the molecules can then be identified by sequencing of the RT-PCR product.

Each step is described below.

(1) Transcription Step

This step is a transcription step in which a cDNA library encoding a candidate protein is transcribed to prepare an mRNA library.

The cDNA library encoding the candidate protein can be prepared by the method for producing a cDNA library described in Patent Document 3. The RNA or mRNA library used for the preparation of a cDNA library may be an RNA or mRNA library extracted from any tissue of any species including prokaryotes, eukaryotes and viruses. Further, the RNA or mRNA library may be an RNA library prepared by transcription of a sequenced genome or a cDNA library; an artificial RNA library prepared by reproduction thereof; or an RNA library prepared by transcribing an artificial cDNA library containing a sequence that does not naturally occur.

The transcription step of transcribing a cDNA library to prepare an mRNA library can be carried out by the method for producing an RNA library described in Patent Document 3.

(2) Assignment Step

This step is an assignment step of preparing an mRNA-protein assignment molecular library from the mRNA library prepared in the transcription step. This step can be carried out by the method described in Patent Document 2 or Patent Document 3. A specific example is described below.

(2-1) Assignment Molecule

In the present description, the assignment molecule (having the same meaning as IVV) means a molecule that assigns the phenotype and the genotype to each other. The assignment molecule is composed of a genotype molecule comprising a nucleic acid having a base sequence reflecting the genotype and a phenotype molecule comprising a protein involved in expression of the phenotype, which genotype molecule and phenotype molecule are linked to each other. The genotype molecule is composed of a base sequence reflecting the genotype in a form that allows translation of the base sequence, and a spacer portion linked thereto. Since such an assignment molecule is described in, for example, Patent Document 2, the molecule will be described below by reference to Patent Document 2.

In the assignment molecule, the portion derived from the phenotype molecule, the portion derived from the spacer molecule and the portion derived from the coding molecule are referred to as the decoded portion, spacer portion and coding portion, respectively. Further, in the genotype molecule, the portion derived from the spacer molecule and the portion derived from the coding molecule are referred to as the spacer portion and the coding portion, respectively.

FIG. 8 in Patent Document 2 roughly shows an example of the constitutions of the assignment molecule, spacer molecule and coding molecule. This assignment molecule is composed of the spacer (referred to as the spacer portion) and the base sequence reflecting the code of the phenotype (referred to as the coding portion). The assignment molecule has a constitution prepared by linking the spacer portion comprising puromycin to the coding molecule by a certain method to provide the genotype molecule, which is then linked to the phenotype molecule on the ribosome in a cell-free translation system. The spacer molecule is composed of: the PEG region whose main component is polyethylene glycol; the CCA region comprising at least puromycin, or puromycin and DNA and/or RNA having 1 or more residues; the donor region comprising at least DNA and/or RNA having 1 or more residues; and the functionalization unit (X) in which the base of at least one residue of DNA and/or RNA is functionally modified. The coding molecule is constituted by: the 3'-end region which is composed of a part of the sequence of the decoded portion and comprises a poly(A) sequence of DNA and/or RNA; 5'-UTR which is composed of DNA and/or RNA and comprises a transcription promoter and a translation enhancer; and the ORF region mainly composed of the sequence of the phenotype molecule. A description is given below by reference to this example, but the present invention is not restricted to the example.

(2-2) Spacer Molecule

The spacer molecule comprises: the donor region, which can be bound to the 3'-end of nucleic acid; the PEG region, which is bound to the donor region and mainly composed of polyethylene glycol; and the peptide acceptor region, which is bound to the PEG region and comprises a group that can be bound to a peptide by transpeptidation.

The donor region which can be bound to the 3'-end of nucleic acid is normally composed of 1 or more nucleotides. The number of nucleotides is usually 1 to 15, preferably 1 to 2. The nucleotides may be either ribonucleotides or deoxyribonucleotides.

The sequence at the 5'-end of the donor region influences the ligation efficiency. For ligation between the coding portion and the spacer portion, the sequence needs to comprise at least 1 residue. For the acceptor having a poly(A) sequence, the sequence at the 5'-end of the donor region preferably comprises at least 1 residue of dC (deoxycytidylic acid) or the 2 residues dCdC (dideoxycytidylic acid). The order of preference of the type of the base is as follows: C>U/T>G>A.

The PEG region comprises polyethylene glycol as the major component. The term "comprises as the major component" herein means that the total number of nucleotides contained in the PEG region is not more than 20 bp, or the average molecular weight of the polyethylene glycol is not less than 400. The term preferably means that the total number of nucleotides is not more than 10 bp, or the average molecular weight of the polyethylene glycol is not less than 1,000.

The average molecular weight of the polyethylene glycol in the PEG region is usually 400 to 30,000, preferably 1,000 to 10,000, more preferably 2,000 to 8,000. In cases where the molecular weight of the polyethylene glycol is less than about 400, assignment translation of the genotype molecule comprising the spacer portion derived from this spacer molecule may require posttreatment after the assignment translation in some cases (Liu, R., Barrick, E., Szostak, J. W., Roberts, R. W. (2000) Methods in Enzymology, vol. 318, 268-293). On the other hand, in cases where PEG having a molecular weight of not less than 1,000, preferably not less than 2,000 is used, the assignment can be achieved highly efficiently only by assignment translation, so that posttreatment after the translation is not necessary. Further, as the molecular weight of the polyethylene glycol increases, the stability of the genotype molecule tends to increase. In cases where the molecular weight is not less than 1,000, the stability is especially excellent, while in cases where the molecular weight is not more than 400, the properties are not largely different from those of a DNA spacer, which may lead to instability.

The peptide acceptor region is not restricted as long as it can be bound to the C-terminus of a peptide, and examples of the region which may be used include puromycin, 3'-N-aminoacylpuromycin aminonucleoside (PANS-amino acid), such as PANS-Gly, wherein the amino acid portion is glycine; PANS-Val, wherein the amino acid portion is valine; PANS-Ala, wherein the amino acid portion is alanine; and PANS-all amino acids, which corresponds to all the amino acids. Further, 3'-N-aminoacyladenosine aminonucleoside (AANS-amino acid) in which the amino group of 3'-aminoadenosine is chemically bound to the carboxyl group of an amino acid via an amide bond formed as a result of dehydration condensation, such as AANS-Gly, wherein the amino acid portion is glycine; AANS-Val, wherein the amino acid portion is valine; AANS-Ala, wherein the amino acid portion is alanine; and AANS-all amino acids, which corresponds to all the amino acids; may be used. Further, a nucleoside or a nucleoside bound to an amino acid via an ester bond may also be used. Further, any compound having a binding mode that allows chemical binding of a substance comprising a nucleoside or a chemical structural skeleton similar to a nucleoside with a substance comprising an amino acid or a chemical structural skeleton similar to an amino acid may be used.

The peptide acceptor region is preferably composed of puromycin or a derivative thereof, or puromycin or a derivative thereof and 1 residue or 2 residues of deoxyribonucleotide(s) or ribonucleotide(s). The derivative herein means a derivative that can be bound to the C-terminus of a peptide in a protein translation system. The puromycin derivative is not restricted to one having the complete puromycin structure, and also includes one which partially lacks the puromycin structure. Specific examples of the puromycin derivative include PANS-amino acids and AANS-amino acids.

The peptide acceptor region may have a structure which comprises only puromycin, but the region preferably has in its 5'-side a base sequence of DNA and/or RNA having 1 or more residues. Preferred examples of the sequence include sequences of dC-puromycin and rC-puromycin, and more preferred examples of the sequence include sequences of dCdC-puromycin, rCrC-puromycin, rCdC-puromycin and dCrC-puromycin. As the sequence, a CCA sequence that mimics the 3'-end of an aminoacyl-tRNA (Philipps, G. R. (1969) Nature 223, 374-377) is suitable. The order of preference of the type of the base is as follows: C>U/T>G>A.

(2-3) Coding Molecule

The coding molecule is a nucleic acid comprising: the 5'-untranslated region comprising a transcription promoter and a translation enhancer; the ORF region which is linked to the 3'-side of the 5'-untranslated region and encodes a protein; and the 3'-end region which is linked to the 3'-side of the ORF region and comprises a poly(A) sequence and, as required, a translation-enhancing sequence (e.g., sequence recognized by the restriction enzyme XhoI) at the 5'-side of the poly(A) sequence. The coding molecule constitutes the mRNA library prepared in the transcription step.

The 3'-end region preferably comprises an SNNS sequence (e.g., XhoI sequence) which is followed by a poly(A) sequence in its downstream. As a factor that influences the efficiency of ligation between the spacer molecule and the coding molecule, the poly(A) sequence in the 3'-end region is important. The poly(A) sequence is a continuous poly(A) strand having at least 2 residues of dA and/or rA, and may be either composed of only one of these types of residues or a mixture of these. The sequence is a strand composed of continuous poly(A) having preferably not less than 3 residues, more preferably not less than 6 residues, still more preferably not less than 8 residues.

Examples of factors that affect the efficiency of translation of the coding molecule include the combination of the 5'-UTR, which is composed of the transcription promoter and the translation enhancer, and the 3'-end region comprising the poly(A) sequence. The effect of the poly(A) sequence in the 3'-end region is usually produced with 10 residues or less. The transcription promoter in the 5'-UTR is not restricted and may be T7/T3, SP6 or the like. The transcription promoter is preferably SP6, which is especially preferably used in cases where a sequence comprising an omega sequence or a part of an omega sequence (Ω-like sequence) is employed as the translation enhancer sequence. The translation enhancer is preferably a part of an omega sequence, and the part of an omega sequence preferably comprises a part (O29) of the omega sequence in TMV (Gallie D. R., Walbot V. (1992) Nucleic Acids Res., vol. 20, 4631-4638).

Further, for high translation efficiency, the combination of the XhoI sequence and the poly(A) sequence in the 3'-end region is important. The combination of the part downstream of the ORF region, that is, the XhoI sequence and the affinity tag in the upstream thereof, and the poly(A) sequence is also important. The sequence of the affinity tag is not restricted as long as it is a sequence for using a method for allowing detection of a protein, such as the antigen-antibody reaction. The sequence is preferably the Flag-tag sequence, which is a tag for affinity separation analysis by the antigen-antibody reaction. In terms of the effect of the poly(A) sequence, the translation efficiency can be increased by using an affinity tag such as the Flag-tag together with the XhoI sequence, and by further using the poly(A) sequence attached thereto.

The above constitution effective for increasing the translation efficiency is also effective for increasing the assignment efficiency.

The sequence of the ORF region is not restricted, and examples of the sequence include gene sequences, exon sequences, intron sequences and random sequences, and arbitrary natural and artificial sequences. By using SP6+O29 for the 5'-UTR of the coding molecule and Flag+XhoI+$A_n$ (n=8) for the 3'-end region, the lengths of the 5'-UTR and the 3'-end region become about 60 bp and about 40 bp, respectively, allowing their incorporation into a PCR primer to provide adaptor regions. Therefore, a coding molecule having the 5'-UTR and the 3'-end region can be simply prepared by PCR from an arbitrary vector, plasmid or cDNA library. The coding molecule may allow translation to proceed beyond the ORF region. That is, the ORF region does not need to have a stop codon at its end.

FIG. 10 in Patent Document 2 shows detailed constitution of an example of the coding molecule. The coding molecule is composed of the 3'-end region; 5'-UTR region comprising a transcription promoter and a translation enhancer; and the ORF region which is composed of the sequence information for the decoded portion, that is, which encodes the phenotype protein. Here, the 3'-end region comprises an affinity tag sequence, XhoI sequence and poly A sequence, and the Flag-tag sequence is used. For the 5'-UTR, SP6 as the transcription promoter, and O29, which is a part of the omega sequence, as the translation enhancer are used.

(2-4) Genotype Molecule and Method of Production Thereof

The genotype molecule is formed by linking the 3'-end of the coding molecule to the donor region of the spacer molecule, which coding molecule is a nucleic acid comprising: the 5'-untranslated region comprising a transcription promoter and a translation enhancer; the ORF region which is linked to the 3'-side of the 5'-untranslated region and encodes a protein; and the 3'-end region which is linked to the 3'-side of the ORF region and comprises a poly A sequence.

The coding molecule constituting the genotype molecule is the same as described above about the coding molecule except that the XhoI sequence is not indispensable. However, the coding molecule preferably has the XhoI sequence.

The genotype molecule can be produced by linking the 3'-end of the above coding molecule to the donor region of the spacer molecule by normal ligase reaction. Examples of the reaction conditions normally include a temperature of 4 to 25° C. and a period of 4 to 48 hours, and, in cases where polyethylene glycol having the same molecular weight as the polyethylene glycol in the PEG region of the spacer molecule comprising the PEG region is added to the reaction system, the conditions may be a temperature of 15° C. and a reduced period of 0.5 to 4 hours.

The combination of the spacer molecule and the coding molecule has a large effect on the ligation efficiency. The 3'-end region of the coding portion, which corresponds to the acceptor, preferably has a poly(A) sequence of DNA and/or RNA comprising at least 2 residues, preferably not less than 3 residues, more preferably not less than 6 to 8 residues. Further, the translation enhancer in the 5'-UTR is preferably a partial sequence of the omega sequence (O29; FIG. 10 in Patent Document 2), and the donor region in the spacer portion preferably has at least 1 residue of dC (deoxycytidylic acid) or the 2 residues dCdC (dideoxycytidylic acid). By this, RNA ligase can be used to avoid problems in DNA ligase, and the efficiency can be maintained at 60 to 80%.

It is preferred to link (a) the 3'-end of the coding molecule comprising: the 5'-untranslated region comprising a transcription promoter and a translation enhancer; the ORF region which is linked to the 3'-side of the 5'-untranslated region and encodes a protein; and the 3'-end region which is linked to the 3'-side of the ORF region and comprises a poly A sequence; to (b) the donor region of the spacer molecule according to any one of (1) to (4), which region is composed of RNA, using RNA ligase in the presence of free polyethylene glycol having the same molecular weight as the polyethylene glycol constituting the PEG region in the spacer molecule.

By the addition, upon the ligation reaction, of polyethylene glycol having the same molecular weight as the PEG region of the spacer portion comprising the PEG region, the ligation efficiency is increased to not less than 80 to 90% irrespective of the molecular weight of the polyethylene glycol in the spacer portion, and the separation step after the reaction can be omitted.

(2-5) Assignment Molecule and Method of Production Thereof

The mRNA-protein assignment molecule is formed by linking, by transpeptidation, the above genotype molecule to the phenotype molecule, which is a protein encoded by the ORF region in the genotype molecule.

For example, the assignment molecule may be linked to the phenotype molecule, which is a protein encoded by the ORF region in the genotype molecule, by transpeptidation by translation of the genotype molecule in a cell-free translation system.

The cell-free translation system is preferably the wheat germ system or the rabbit reticulocyte system. The conditions for translation may be those usually employed. Examples of the conditions include a temperature of 25 to 37° C. for a period of 15 to 240 minutes.

In terms of the cell-free translation system, those of *E. coli*, rabbit reticulocytes and wheat germs have so far been studied for use in formation of assignment molecules, and formation of assignment molecules could be confirmed in only the rabbit reticulocyte system (Nemoto, N., Miyamoto- Sato, E., Yanagawa, H. (1997) FEBS Lett. 414, 405; Roberts, R. W, Szostak, J. W. (1997) Proc. Natl. Acad. Sci. USA 94, 12297). However, according to the present embodiment, the wheat germ system can also be used for formation of assignment molecules having the spacer portion comprising the PEG region. Further, although the rabbit reticulocyte system has been impractical because of instability of the genotype molecule and was therefore applied to only genotype molecules having short chain lengths (Roberts, R. W, Szostak, J. W. (1997) Proc. Natl. Acad. Sci. USA 94, 12297; Nemoto, N., Miyamoto-Sato, E., Yanagawa, H. (1997) FEBS Lett. 414, 405), assignment molecules having the spacer portion comprising the PEG region are more stable in the wheat germ system and allow handling of longer chains, which makes the system more practical.

In cases where an "interaction" is realized by cell-free cotranslation, the cell-free translation system may be any system including those of *E. coli*, rabbit reticulocytes and wheat germs. In the in vitro virus method (IVV method), the process of formation of the assignment molecule is rather instable in the *E. coli* system, but the process has been confirmed to be stable in the rabbit reticulocyte system (Nemoto N, Miyamoto-Sato E, Yanagawa H. (1997) FEBS Lett. 414, 405; Roberts R. W, Szostak J. W. (1997) Proc. Natl. Acad. Sci. USA 94, 12297) and even more stable in the wheat germ system (WO 02/46395).

(3) Selection Step

This step is a selection step of selecting mRNA-protein assignment molecules that interact with a target substance from the mRNA-protein assignment molecular library prepared in the assignment step.

The method of selection is not limited as long as an assignment molecule can be used, and may be carried out by a known method. Examples of the method include the selection process described in Patent Document 1.

More specific examples of the method include the following method. A target substance such as a protein, nucleic acid (DNA or RNA), or another substance including a saccharide or lipid, is preliminarily bound to a microplate or beads via covalent bonds or noncovalent bonds, and assignment molecules prepared in the assignment step are added to the resultant, followed by allowing the reaction to proceed at a certain temperature for a certain period of time, and washing the microplate or beads for removal of assignment molecules unbound to the target. Thereafter, the assignment molecules bound to the target are released and recovered.

(4) Amplification Step

This step is an amplification step of preparing a cDNA library encoding the candidate protein by nucleic acid amplification based on the mRNA portion of the mRNA-protein assignment molecule selected in the selection step. The method of amplification is not limited as long as amplification of the nucleic acid based on the mRNA portion of the assignment molecule is possible, and may be carried out by a known method. Examples of the method include a method in which reverse transcription and amplification are carried out by RT-PCR.

In the present invention, in each of a plurality of times of preparation of a cDNA library among the initial preparation of a cDNA library and the round(s) of preparation of a cDNA library in the later amplification step(s), the cDNA library is prepared using a primer(s) having a sequence(s) specific to the time of preparation. By this, after determining the sequences of the nucleic acid portions constituting the libraries, the library from which each sequence is derived can be identified.

The length and the position of the specific sequence are not limited as long as the sequence can be identified after determination of the sequence in a later step. Since, in usual screening, the steps of (1) to (4) are repeated 3 to 5 times, the length may be one that allows identification of 6 times of preparation including the first preparation. In this case, a length of 3 bases is sufficient. On the other hand, for simplifying the identification, a sequence having a length longer than the number of bases that is logically required may be employed. From this viewpoint, the length of the sequence is usually 4 to 10 bases.

The position of this sequence in the primer is not limited as long as the sequence does not inhibit the amplification, and the sequence is usually placed in the 5'-side of the primer.

The preparation of a cDNA library using the primer(s) having a sequence(s) specific to the time of preparation does not necessarily need to be carried out for all of the first preparation and the subsequent rounds, and the preparation may be carried out a number of times that is required for obtaining a significant result in the later-described detection. Usually, 3 to 6 cDNA libraries each containing a sequence specific to the time of preparation may be provided.

The part in which the specific sequence contained in the primer is utilized to analyze the sequence is described below.

In the present invention, cDNA libraries each prepared using a primer(s) having a sequence(s) specific to the time of preparation are mixed together, and sequences in the resulting cDNA library mixture are determined.

The mixing ratios of the cDNA libraries may be determined in consideration of the performance of the sequencer used for determination of sequences, and it is preferred to increase the ratios of the libraries obtained by earlier times of the preparation, in which the sequence of interest is not enriched. That is, the mixing ratio of the cDNA library obtained by an earlier time of preparation is preferably not less than the mixing ratio of the cDNA library obtained by the subsequent time of preparation. Since the enrichment ratio of the prey in each time of preparation is usually within the range of about 10 to 100, the amount of the cDNA library obtained by an earlier time of preparation is preferably 1 to 100 times as much as the amount of the cDNA library obtained by the subsequent time of preparation in consideration of the scale of sequencing. By this, the analysis can be efficiently carried out.

The method of sequencing is not limited as long as sequences contained in the mixture (sequences encoding proteins, including the sequences specific to the times of preparation) can be determined. Since the number of molecules to be sequenced increases by the mixing, the method preferably uses the so-called next generation sequencer or a sequencer employed for high-throughput sequencing.

The thus determined sequences are subjected to measurement of the number of sequences (which corresponds to the number of molecules) encoding the same candidate protein for each time of preparation based on the sequence(s) specific to the time of preparation. This can be carried out by a method using a computer, which is known as the in silico analysis.

Based on the number measured for each time of preparation in such a manner, a sequence (molecule) that significantly increased as the preparation rounds proceeded is detected as a protein that interacts with the target substance. The judgment of the increase may also be carried out using a part of the data for the times of preparation. For example, in cases where the first data and the data for the rounds 1 to 4 are obtained, the data for the rounds 2 to 4, which correspond to the latter half, may be used, or data in which those for an intermediate round(s) is/are omitted, such as the first data and the data for the rounds 2 and 4, may be used.

The increase in the sequence (molecules) is preferably evaluated by a statistical method. Examples of the statistical method include Fisher's exact probability test.

The target substance is, for example, a protein. In cases of a protein, protein-protein interaction can be detected.

In techniques for analyzing protein-protein interaction using a conventional mRNA display technique such as the IVV method, a large cost is required for additional verification experiments such as a quantitative real-time PCR assay for judgment of false positives. By the present invention, such a cost can be reduced. Since, in the conventional methods, determination of the type of the prey protein is carried out using the result of sequencing for each round, the cloning step in this process decreases the analysis efficiency, leading to production of a large number of false negatives. In the present invention, such false negatives can be reduced. In the present invention, instead of carrying out sequencing for each round, a mixture of libraries obtained in a plurality of rounds is subjected to sequencing, while evaluation of sequences can be carried out for each round. Therefore, it is thought that the error of detection of the change in each round can be minimized, and that accurate evaluation of the enrichment is possible in screening by the IVV method.

An examples of the present invention is specifically described below, but the Example should be regarded merely as a help to specifically recognize the present invention. Therefore, the scope of the present invention is not limited by the Example below. The present Example describes a specific case where the present invention was actually applied, and results of comparison of the present invention with a conventional method in which sequencing is carried out for each round.

EXAMPLES

1. Outline

Four rounds of the selection process by the IVV method was carried out in an attempt to extract proteins that interact with Irf7 (Interferon regulatory factor 7) from a random fragment library derived from mouse spleen.

2. Selection by IVV Method

Preparation of Prey Library

An RNA library to be used for mRNA display was prepared according to a method reported previously (Miyamoto-Sato, E., et al. (2005) Genome Res, 15, 710-717; Miyamoto-Sato, E., et al. (2003) Nucleic Acids Res, 31, e78.), from poly(A)+mRNA extracted from a C57BL/6 mouse. First, random priming of the poly(A)+mRNA was carried out, and ligation-mediated amplification, and multistep PCR for in vitro expression were carried out. The resulting PCR product (SP6-Ω-T7-Flagment-Kpn1-FLAG-A[8]) was purified with QIAquick PCR Purification Kit (Qiagen), and transcribed with m7G(5')ppp(5')G RNA Capping Analog (Ambion) using RiboMAX Large Scale RNA Production System-SP6 (Promega). mRNA was purified using RNeasy 96 BioRobot 8000 Kit (Qiagen), and a PEG-Puro spacer was ligated to the 3'-end of the mRNA using T4RNA ligase (Promega). Purification was then carried out again.

Preparation of Bait

The DNA for the bait was prepared according to an earlier report (Miyamoto-Sato, E., et al. (2005) Genome Res, 15, 710-717; Miyamoto-Sato, E., et al. (2003) Nucleic Acids Res, 31, e78.). The structure of the cDNA construct prepared by multistep PCR (SP6-(O')-T7-Irf7-CBP-zz-His) contains the entire coding region of mouse Irf7. The PCR product produced using QIAquick PCR Purification Kit (Qiagen) was transcribed into mRNA using RiboMax Large Scale RNA Production System-SP6 (Promega) together with m7G (5')ppp(5')G RNA Capping Analog, and purified using RNeasy 96 BioRobot 8000 Kit (Qiagen).

In Vitro Translation and Selection

The prey mRNA library and the bait Irf7 mRNA were cotranslated in a cell-free translation system using a wheat germ extract (Promega). In this process, puromycin attached to the 3'-end of the mRNA is covalently linked to the C-terminus of the protein translated from the mRNA, to complete an IVV molecule. Thereafter, a single stage (or 2 stages, only in the case of the fourth round) of purification using the tagged bait protein (Rigaut, G., et al. (1999) Nat Biotechnol, 17, 1030-1032.) was carried out. After each selection round, the prey mRNA is amplified by RT-PCR, and transcription/translation reactions are then carried out, followed by performing the next-round selection. A negative control experiment was carried out under the same conditions except that the bait protein was absent.

Preparation of Sample for Sequencing with 454 GS FLX

In order to identify, after sequencing with 454 GS FLX, the round from which each sequence was derived, amplification of the initial to 4th-round mRNA libraries by RT-PCR was carried out using barcode primers each having a unique 4-base sequence as shown in Table 1 below.

TABLE 1

| Barcode primers for RT-PCR | | |
|---|---|---|
| Amplification for initial library | Forward | ACTA+TGCGGCCGCGAATTCC (SEQ ID NO: 1) |
| | Reverse | TAGT+GTCGTCATCGTCCTTGTAGTC (SEQ ID NO: 2) |
| Amplification after 1st round | Forward | AGTG+TGCGGCCGCGAATTCC (SEQ ID NO: 3) |
| | Reverse | CACT+GTCGTCATCGTCCTTGTAGTC (SEQ ID NO: 4) |
| Amplification after 2nd round | Forward | CAGC+TGCGGCCGCGAATTCC (SEQ ID NO: 5) |
| | Reverse | GCTG+GTCGTCATCGTCCTTGTAGTCA (SEQ ID NO: 6) |
| Amplification after 3rd round | Forward | CGCA+TGCGGCCGCGAATTCC (SEQ ID NO: 7) |
| | Reverse | TGCG+GTCGTCATCGTCCTTGTAGTCA (SEQ ID NO: 8) |
| Amplification after 4th round | Forward | CTCG+TGCGGCCGCGAATTCC (SEQ ID NO: 9) |
| | Reverse | CGAG+GTCGTCATCGTCCTTGTAGTCA (SEQ ID NO: 10) |

The DNA samples amplified with the barcode primers were purified using QIAquick PCR Purification Kit (Qiagen). Thereafter, the enrichment of each sample was measured using NanoDrop. Finally, the samples obtained in the initial preparation and the rounds 1 to 4 were mixed at ratios of 20:10:7:2:1 (ratios of enrichment). The sample for the negative control experiment was prepared by the same method. Finally, the sample from the initial library and 2 mixture samples were sequenced using the GS FLX 454 (Roche) sequencer.

As a result of the sequencing, 206,322 reads were obtained from the bait (+) library; 304,504 reads were obtained from the bait (−) library; and 277,833 reads were obtained from the initial library. Among these, the selection round could be identified for 177,935 reads, 278,816 reads and 238,683 reads, respectively, based on the barcode region. These reads were mapped to the mouse genome using BLAT, and, as a result, it could be confirmed that 47,849 reads of the bait (+) library, 63,306 reads of the bait (−) library, and 102,092 reads of the initial library show appropriate matching with the genome. Thus, these were used in the subsequent in silico analysis.

2.2 In Silico Analysis

Counting and Statistical Analysis of Regions by Mapping to Genome

First, decoding of the 4 bases in the round-specific portion present in the end of each cDNA sequence was carried out to judge the round from which each read was derived. Subsequently, mapping of the processed reads to a masked genomic sequence was carried out using BLAT under the following conditions: match length ≥30 bp and identity ≥95%. The frequencies of the mapped reads in each selection round were calculated for each base position on the genome, and compared with the results for the initial library and the negative control. Further, positions that showed higher frequencies than in the initial library and the negative control were subjected to a statistical test (Fisher's exact probability test). In cases where a statistically significant (p<0.001) difference from the initial library and the negative control was found, the region was regarded as a region showing bait-specific enrichment. Among the regions showing significant enrichment, continuous regions were combined into single regions, and regarded as single interaction regions (IRs).

Figure 2:
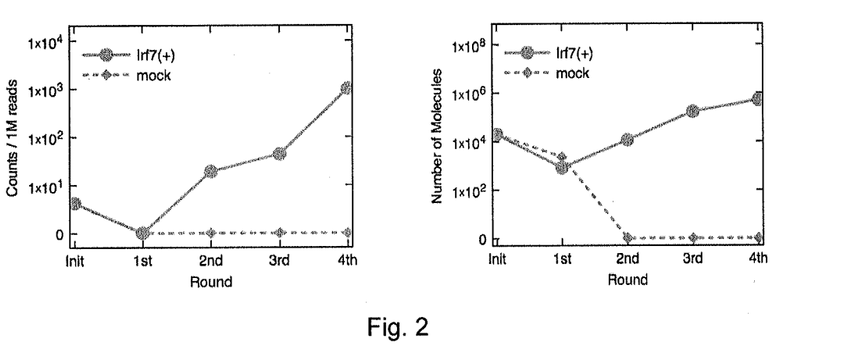
FIG. 2 illustrates comparison of quantitativeness of data between the method of the present invention (left) and a conventional method (right). The left panel illustrates changes in the read frequency in the selection rounds, and the right panel illustrates the results of measurement of the number of molecules in this experiment.
Figure 3:
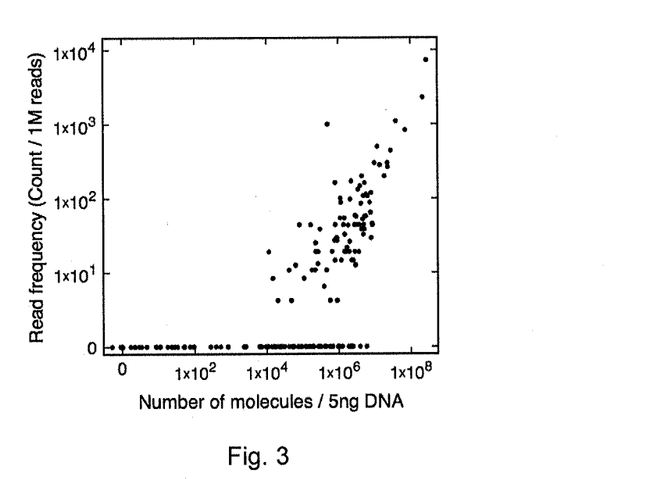
FIG. 3 illustrates comparison of quantitativeness of data between the method of the present invention and a conventional method. The read frequency (the ordinate) and the result of measurement of the number of molecules in the experiment (the abscissa) in each round are shown for 21 regions.

Confirmation of Quantitativeness and Effectiveness Based on Comparison with Real-Time PCR In order to confirm the quantitative performance of the present method, 21 regions whose reads were obtained from a plurality of rounds and that were found to be overlapping with the RefSeq region were randomly extracted, and subjected to a real-time PCR assay as described below. First, the frequencies of reads on the genome were calculated for each selection round. These frequencies were based on the numbers of reads mapped on the genomic sequence. FIG. 2 shows an example of comparison between the frequencies calculated from the results of sequencing (FIG. 2 (left)) and the numbers of molecules quantified by real-time PCR (FIG. 2 (right)). Based on visual observation, the data obtained by the present method showed results well consistent with the quantitative results obtained by the real-time PCR. For further confirmation, the correlation coefficient between these two data sets was calculated (FIG. 3), and the correlation coefficient was statistically confirmed to be significantly high (Pearson's correlation coefficient=0.92). Further, it was confirmed that, among the regions judged to be positive by the present method, 87.5% (⅞) of those were judged to be positive also by the real-time PCR, and that, among the regions judged to be false positive by the real-time PCR, only 8% (1/12) of those were judged to be positive by the present method.

Real-Time PCR Assay

A real-time PCR assay was carried out using 7300 Real-Time PCR System (Applied Biosystems) according to a standard protocol. The assay was carried out using 25 μl of a reaction mixture containing 5 ng of a DNA template derived from the prey library, 10 μM/0.5 μl each of primers (a forward primer and a reverse primer), and 12.5 μl of Power SYBR Green PCR Master Mix (Applied Biosystems). Measurement of the sample was carried out twice, and the average of the measured values was employed.

High-Throughput Determination of Interacting Regions

As described above, a significant correlation could be confirmed between the number of reads obtained by the present method and the number of molecules measured by real-time PCR. Therefore, taking advantage of the quantitative performance of the present method, enriched regions with statistical significance were systematically determined. Statistical significance of enrichment was tested using Fisher's exact probability test on 2×2 contingency tables. Each contingency table is composed of the numbers of reads obtained in bait (+) and bait (−) experiments on a certain region in a certain selection round, and the total number of reads obtained in each experiment. In addition, comparison between the initial library and the certain round was carried out by the same method. As a result, 466 prey regions on the genome were determined under the condition of p-value<0.001.

2.3 Comparison with Conventional Method

Effect on Reduction of False Positives

Based on the result of judgment of the above-described randomly selected regions (for only cases where reads were obtained in a plurality of rounds and primers could be designed in the RefSeq region) by real-time PCR, the ratio of 42.9% (9/21) can be regarded as the ratio of positive regions in the library and as the result of a method where sequencing results for each round are judged by real-time PCR (conventional method). In the present Example, among the regions judged to be positive by the method of the present invention (IVV-HiTSeq method), the ratio of regions judged to be positive also in quantitative real-time PCR was 87.5% (=⅞). Therefore, it is thought that, by using the IVV-HiTSeq method, interaction molecules can be identified with higher reliability as compared to the conventional method.

Effect on Reduction of False Negatives

Figure 4:
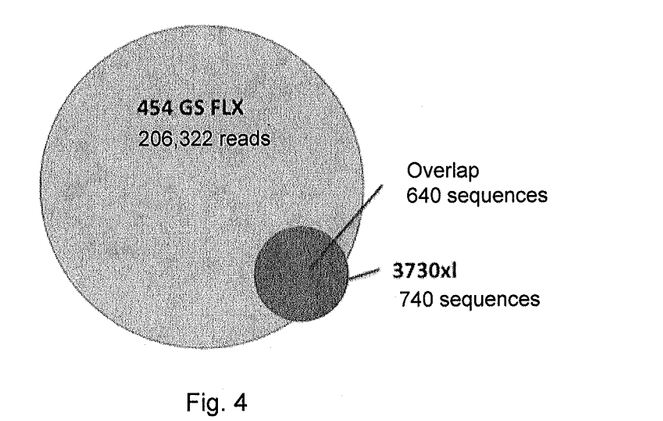
FIG. 4 illustrates the overlap between sequences obtained by the method of the present invention (454 GS FLX) and sequences obtained by a conventional method (3730xl).

Since, in analysis of the same library using Irf7 as the bait, 640 sequences (86.5%) out of the 740 sequences determined by the sequencing method using the product of each round could be obtained also by the IVV-HiTSeq method, it was shown that the result by the IVV-HiTSeq method covers almost the entire result obtained by the conventional method (Table 2, FIG. 4).

Further, among the 479 regions judged to be positive by the IVV-HiTSeq method, only 72 regions could be obtained by the conventional method. This means that the remaining 423 regions can be obtained only by the IVV-HiTSeq method, indicating a high detection capacity of the IVV-HiTSeq method.

Further, since even the 72 overlapping regions cannot be confirmed to be truly positive based only on the clones obtained by sequencing of the amplification product of each round, a test needs to be additionally carried out by a quantitative real-time PCR assay or the like. The present Example corresponded to not less than 4790 (479×number of rounds×2) times of real-time quantitative PCR assays, and it was shown that the efficiency of post selection is remarkably high as compared to the analysis based on determination of sequences in each round followed by quantitative real-time PCR.

TABLE 2

Comparison of results of IVV-HiTSeq method and conventional method

|  | IVV-HiTSeq method | Conventional method |
| --- | --- | --- |
| Number of sequences (Number of clones or reads) | 206,322 | 740 |
| Positive judgment | 479 | 72 |

INDUSTRIAL APPLICABILITY

A method for detecting an interaction, which method can solve not only the problem of false negatives but also the problem of false positives, is provided.

The invention claimed is:

1. A method for detecting a protein(s) that interact(s) with a target substance(s), said method comprising:

(1) a transcription step of transcribing a cDNA library encoding a candidate protein(s) to prepare an mRNA library;

(2) an assignment step of preparing an mRNA-protein assignment molecular library from said mRNA library prepared in the transcription step;

(3) a selection step of selecting an mRNA-protein assignment molecule(s) that interact(s) with a target substance(s) from the mRNA-protein assignment molecular library prepared in the assignment step;

(4) an amplification step of preparing a cDNA library encoding the candidate protein(s) by nucleic acid amplification based on the mRNA portion(s) of said mRNA-protein assignment molecule(s) selected in the selection step; and (5) repeating Steps (1) to (4) using said cDNA library prepared in the amplification step; wherein said method comprises:

(a) preparing, in each of a plurality of times of preparation of a cDNA library among the initial preparation of a cDNA library and the round(s) of preparation of a cDNA library in the later amplification step(s), the cDNA library using a primer(s) having a sequence(s) specific to the time of preparation;

(b) mixing the cDNA libraries prepared using said primers having sequences specific to the times of preparation, and determining sequences in the cDNA library mixture;

(c) subjecting the determined sequences to measurement of the number(s) of molecules encoding the same candidate protein(s) for each time of preparation based on the sequence(s) specific to the time of preparation; and (d) detecting, as the protein(s) that interact(s) with said target substance(s), a candidate protein(s) encoded by a molecule(s) that significantly increase(s) as the preparation rounds proceed.

2. The method according to claim 1, wherein, in Step (b), the mixing ratio of the cDNA library obtained by an earlier time of preparation is not less than the mixing ratio of the cDNA library obtained by the subsequent time of preparation.

3. The method according to claim 1, wherein said sequence specific to each time of preparation has a length of 4 to 10 bases.

4. The method according to claim 1, wherein said primer has said sequence specific to the time of preparation at the 5'-end.

5. The method according to claim 1, wherein the number of cDNA libraries mixed in Step (b) is not less than 3.

6. The method according to claim 1, wherein the cDNA libraries mixed in Step (b) comprise the initial cDNA library.

7. The method according to claim 1, comprising evaluating the increase in the molecules in Step (d) by a statistical method.

8. The method according to claim 1, wherein said target substance is a protein.

* * * * *

SEQUENCE LISTING

<160> NUMBER OF SEQ ID NOS: 10

<210> SEQ ID NO 1
<211> LENGTH: 20
<212> TYPE: DNA
<213> ORGANISM: Artificial sequence
<220> FEATURE:
<223> OTHER INFORMATION: forward primer for initial amplification

<400> SEQUENCE: 1
actatgcggc cgcgaattcc                                                    20

<210> SEQ ID NO 2
<211> LENGTH: 25
<212> TYPE: DNA
<213> ORGANISM: Artificial seequence
<220> FEATURE:
<223> OTHER INFORMATION: reverse primer for initial amplification

<400> SEQUENCE: 2
tagtgtcgtc atcgtccttg tagtc                                              25

<210> SEQ ID NO 3
<211> LENGTH: 20
<212> TYPE: DNA
<213> ORGANISM: Artficial sequence
<220> FEATURE:
<223> OTHER INFORMATION: forward primer for 1st round amplification

<400> SEQUENCE: 3
agtgtgcggc cgcgaattcc                                                    20

<210> SEQ ID NO 4
<211> LENGTH: 25
<212> TYPE: DNA
<213> ORGANISM: Artificial sequence
<220> FEATURE:
<223> OTHER INFORMATION: reverse primer for 1st round amplification

<400> SEQUENCE: 4
cactgtcgtc atcgtccttg tagtc                                              25

<210> SEQ ID NO 5
<211> LENGTH: 20
<212> TYPE: DNA
<213> ORGANISM: Artficial sequence
<220> FEATURE:
<223> OTHER INFORMATION: forward primer for 2nd round amplification

<400> SEQUENCE: 5
cagctgcggc cgcgaattcc                                                    20

<210> SEQ ID NO 6
<211> LENGTH: 26
<212> TYPE: DNA
<213> ORGANISM: Artificial sequence
<220> FEATURE:
<223> OTHER INFORMATION: reverse primer for 2nd round amplification

<400> SEQUENCE: 6
gctggtcgtc atcgtccttg tagtca                                             26

<210> SEQ ID NO 7
<211> LENGTH: 20
<212> TYPE: DNA
<213> ORGANISM: Artficial sequence -continued

```
<220> FEATURE:
<223> OTHER INFORMATION: forward primer for 3rd round amplification

<400> SEQUENCE: 7
cgcatgcggc cgcgaattcc                                              20

<210> SEQ ID NO 8
<211> LENGTH: 26
<212> TYPE: DNA
<213> ORGANISM: Artificial sequence
<220> FEATURE:
<223> OTHER INFORMATION: reverse primer for 3rd round amplification

<400> SEQUENCE: 8
tgcggtcgtc atcgtccttg tagtca                                       26

<210> SEQ ID NO 9
<211> LENGTH: 20
<212> TYPE: DNA
<213> ORGANISM: Artficial sequence
<220> FEATURE:
<223> OTHER INFORMATION: forward primer for 4th round amplification

<400> SEQUENCE: 9
ctcgtgcggc cgcgaattcc                                              20

<210> SEQ ID NO 10
<211> LENGTH: 26
<212> TYPE: DNA
<213> ORGANISM: Artificial sequence
<220> FEATURE:
<223> OTHER INFORMATION: reverse primer for 4th round amplification

<400> SEQUENCE: 10
cgaggtcgtc atcgtccttg tagtca                                       26
```